US006937896B1

(12) United States Patent
Kroll

(10) Patent No.: US 6,937,896 B1
(45) Date of Patent: Aug. 30, 2005

(54) SYMPATHETIC NERVE STIMULATOR AND/OR PACEMAKER

(75) Inventor: Mark W. Kroll, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 514 days.

(21) Appl. No.: 10/087,404

(22) Filed: Feb. 26, 2002

(51) Int. Cl.$^7$ ............................................. A61N 1/368
(52) U.S. Cl. ........................................................ 607/9
(58) Field of Search .............................. 600/373, 374, 600/377, 393, 509, 526; 607/4–7, 24, 44, 607/119, 122, 123

(56) References Cited

U.S. PATENT DOCUMENTS

| | | |
|---|---|---|
| 4,543,954 A | 10/1985 | Cook et al. |
| 4,936,304 A | 6/1990 | Kresh et al. |
| 5,199,428 A | 4/1993 | Obel et al. |
| 5,203,326 A | 4/1993 | Collins |
| 5,334,221 A | 8/1994 | Bardy |
| 5,356,425 A | 10/1994 | Bardy et al. |
| 5,507,784 A | 4/1996 | Hill et al. |
| 5,522,854 A | 6/1996 | Ideker et al. |
| 5,578,061 A | 11/1996 | Stroetmann et al. |
| 5,700,282 A | 12/1997 | Zabara |
| 5,916,239 A | 6/1999 | Geddes et al. |
| 5,928,272 A | 7/1999 | Adkins et al. |
| 6,006,134 A | 12/1999 | Hill et al. |
| 6,073,048 A | 6/2000 | Kieval et al. |
| 6,314,323 B1 * | 11/2001 | Ekwall .......................... 607/23 |
| 6,690,971 B2 * | 2/2004 | Schauerte et al. ............ 607/17 |

FOREIGN PATENT DOCUMENTS

WO    WO 93/21824    11/1993

OTHER PUBLICATIONS

Fany A. Kralios, Luis Martin, Mary Jo Burgess & Kay Millar, "Local ventricular repolarization changes due to sympathetic nerve-branch stimulation," American Journal of Physiology, vol. 228, No. 5, May 1975, pp. 1621-1626.

Benjamin J. Scherlag, Ph.D., Wm. Yamanashi, Ph.D., Patrick Schauerte, M.D., Michael A. Scherlag, M.D., Warren M. Jackman, M.D., & Ralph Lazzara, M.D., "Selective Sympathetic Control of Either Heart Rate or A-V Automaticity, Conduction and Ventricular Conlractility Using Endovascular Stimulation," Naspe Abstracts, Pace, vol. 2, Apr. 2000, Part II, p. 676.

William P. Geis, B.S. & Michael P. Kaye, M.S., MD, "Distribution of Sympathetic Fibers in the Left Ventricular Epicardial Plexus of the Dog," Circulation Research, vol. XXIII, No. 2, Aug. 1968, pp 165-170.

Hiroshi Inoue & Douglas P. Zipes, "Changes in Atrial and Ventricular Refractoriness and in Atrioventricular Nodal Conduction Produced by Combinations of Vagal and Sympathetic Stimulation That Result in a Constant Spontaneous Sinus Cycle Length," Circulation Research, vol. 60, No. 6, Jun. 1987, pp. 942-951.

(Continued)

Primary Examiner—Jeffrey R. Jastrzab
Assistant Examiner—Frances P. Oropeza

(57) ABSTRACT

An exemplary method for increasing cardiac output that includes detecting a need for increased cardiac output and delivering electrical signals to a first electrode proximate to a left sympathetic nerve pathway and a second electrode proximate to a right sympathetic nerve pathway to stimulate sympathetic nerves and thereby increase cardiac output. A device for performing such an exemplary method. Other methods and/or devices are also disclosed.

28 Claims, 10 Drawing Sheets

OTHER PUBLICATIONS

Koonlawee Nademanee, MD, Richard Taylor, MD, William E. Bailey, MD, Daniel E. Reiders, MD, Erol M. Kosar, MD, "Treating Electrical Storm Sympathetic Blockade Versus Advanced Cardiac Life Support-Guided Therapy," Circulation, Aug. 15, 2000, pp. 742-747.

Anil K. Bhandari, MD, Melvin M. Scheinman, MD, Fred Morady, MD, John Svinarich, MD, Jay Mason, MD & Roger Winkle, MD, "Efficacy of left cardiac sympathectomy in the treatment of patients with the long QT syndrome," Circulation, vol. 70, No. 6, Dec. 1984, pp. 1018-1023.

G. Michael Vincent, MD, J.A. Abildskov, MD, M.J. Burgess MD, Kay Millar, MD, "Autonomic Manipulation in the Inherited Long QT-Recurrent Syncope Syndromes," The American Journal of CARDIOLOGY, vol. 33, Jan.1974, p. 174.

Walter C. Randall, Mathias Szenlivanyi, John B. Pace, James S. Wechster & Michael P. Kaye, "Patterns of Sympathetic Nerve Projections onto the Canine Heart," Circulation Research, vol. XXII, No. 3, Mar. 1968, pp. 315-323.

Frank Yanowitz, BA, James B. Preston, MD & J.A. Abildskov, MD, "Functional Distribution of Right and Left Stellate Innervation to the Ventricles: Production of Neurogenic Electrocardiographic Changes by Unilateral Alteration of Sympathelic Tone," Circulation Research, vol. XVIII, Apr. 1966, pp. 416-428.

James B. Martins & Douglas P. Zipes, "Effects of Sympathelic and Vagal Nerves on Recovery Properties of the Endocardium and Epicardium of the Canine Left Ventricle," Circulation Research vol. 46, No. 1, Jan. 1980, pp. 100-110.

Yrsa Bergmann Sverrisdotur, PhD, Bengl Rundqvist, MD, PhD, Gudmundur Johannsson, MD, PhD, Mikael Elam, MD, PhD, "Sympathetic Neural Burst Amplitude Distribution—A More Specific Indicator of Sympathoexcitation in Human Heart Failure," Circulation, Oct. 24, 2000, pp. 2076-2081.

Gregory W. Thompson, BSc, James M. Levett, MD, Scott M. Miller, MD, Michael R.S. Hill, PhD, William G. Meffert, MD, Ronald J. Kolata, DVM, Michael F. Clem, DVM, David A. Murphy, DVM, MD, & J. Andrew Armour, MD, PhD, "Bradycardia Induced by Intravascular Versus Direct Stimulation of the Vagus Nerve," 1998 The Society of Thoracic Surgeons, published by Elsevier Science Inc., pp. 637-642.

I.M. Ali, MD, C.K. Butler, MD, J.A. Armour, MD, PhD, & D.A. Murphy, MD, "Modification of Supraventricular Tachyarrhythmias by Stimulating Atrial Neurons," 1990 by The Society of Thoracic Surgeons, pp. 251-256.

Patrick Schauerte, MD, Benjamin J. Scherlag, PhD, FACC, Michael A. Scherlag, MD, Sunil Goli, MD, Warren M. Jackman, MD, FACC, Ralph Lazzara, MD, FACC, "Ventricular Rate Control During Atrial Fibrillation by Cardiac Parasympathetic Nerve Stimulation: A Transvenous Approach," Journal of the American College of Cardiology, vol. 34, No. 7, pp. 2043-2050.

Xiaohong Zhou, MD, Frank L. Vance IV, Anthony L. Sims, Catherine M. Sreenan, BS, Raymond E. Ideker, MD, PhD, "Prevention of High Incidence of Neurally Mediated Ventricular Arrhythmias by Afferent Nerve Stimulation in Dogs," Circulation, Feb. 22, 2000 (American Heart Association, Inc.), pp. 819-824.

Chuen-Wang Chiou, MD, John N. Eble, MD, Douglas P. Zipes, MD, "Efferent Vagal Innervation of the Canine Atria and Sinus and Atrioventricular Nodes—The Third Fat Pad," Circulation, vol. 95. No. 11, Jun. 3, 1997, pp. 2573-2584.

Ralph Lazzara, Benjamin J. Scherlag, Morton J. Robinson, & Philip Samet, "Selective In Situ Parasympathetic Control of the Canine Sinoatrial and Atrioventricular Nodes," Circulation Research, vol. XXXII, Mar. 1973, pp. 393-401.

Shih-Ann Chen, MD, Chem-En Chiang, MD, Ching-Tai Tai, MD, Zu-Chi Wen, MD, Shih-Huang Lee, MD, Chuen-Wang Chiou, MD, Yu-Ann Ding, MD & Mau-Song Chang, MD, "Intracardiac Stimulation of Human Parasympathetic Nerve Fibers Induces Negative Dromotropic Effects: Implication with the Lesions of Radiofrequency Catheter Ablation," Journal of Cardiovascular Electrophysiology, vol. 9, No. 3, Mar. 1998, pp. 245-252.

Don W. Wallick & Paul J. Martin, "Separate parasympathetic control of heart rate and atrioventricular conduction of dogs," 1990 the American Physiological Society, pp. H536-H542.

J.A. Abildskov, MD, "Adrenergic effects on the QT interval of the electrocardiogram," American Heart Journal, Aug., 1976. vol. 92, No. 2, pp. 210-216.

* cited by examiner

METHOD FOR STIMULATING SYMPATHETIC NERVES

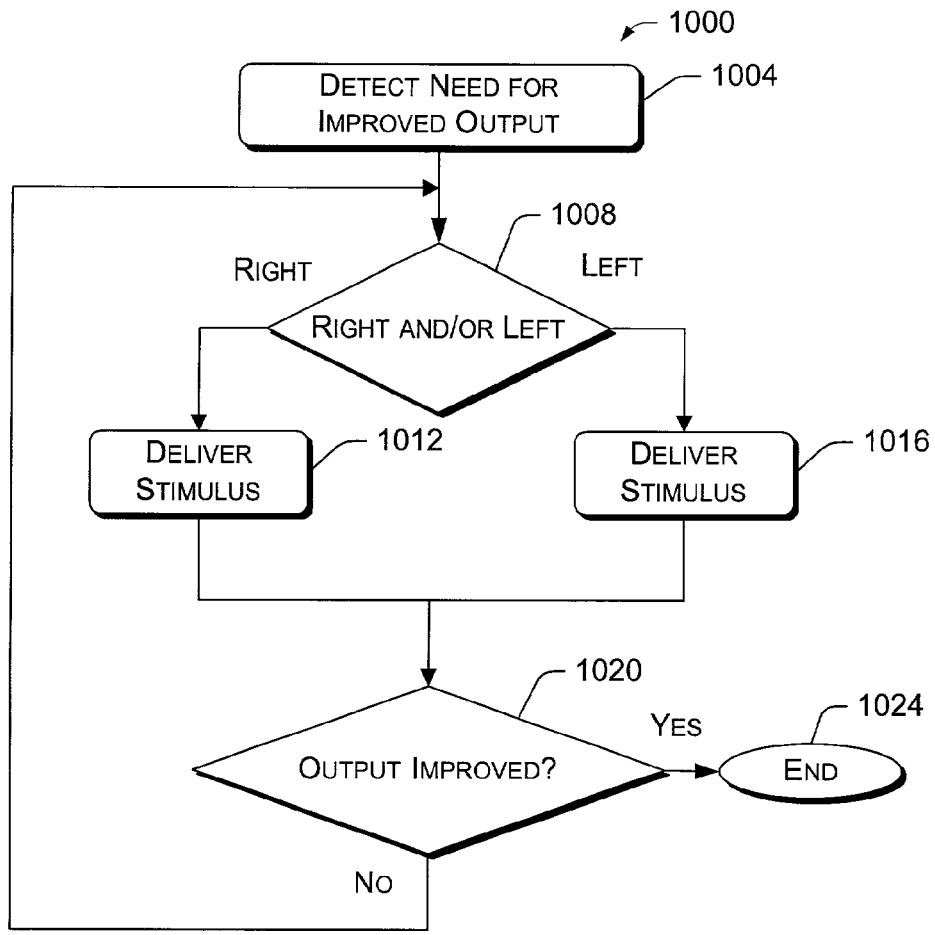

SYMPATHETIC NERVE STIMULATOR AND/OR PACEMAKER

TECHNICAL FIELD

Exemplary methods and/or devices presented herein generally relate to cardiac pacing and/or stimulation therapy. Various exemplary methods and/or devices concern stimulating nerves to control cardiac output in a patient experiencing, or at risk of experiencing, congestive heart failure.

BACKGROUND

Some view sympathetic activation, with its accompanied increased release and diminished reuptake of norepinephrine from myocardial sympathetic nerve terminals, as a rather acute response to circulatory stress. See, e.g., Frantz, "Beta blockade in patients with congestive heart failure," *Postgraduate Medicine*, 108(3), 103–118 (2000). Norepinephrine, a catecholamine released by sympathetic nerves, causes an increase in heart rate and inotropy (contractility) and hence cardiac output. Frantz explains that "[i]n a teleological sense, an acute increase in sympathetic drive was advantageous for our ancestors. When they were being pursued by a tiger or bleeding from a wound, increasing heart rate, peripheral tone, and myocardial contractility allowed them to reach safety or maintain central perfusion". However, chronic sympathetic activation may cause a progressive deterioration in cardiac output. In addition, uncontrollable sympathetic surges can increase the risk of fatal arrhythmia. Thus, sympathetic activation has both beneficial attributes and detrimental attributes. As described below, selective and/or controllable activation of sympathetic neurons may increase beneficial attributes while diminishing detrimental attributes.

SUMMARY

An exemplary method for increasing cardiac output that includes detecting a need for increased cardiac output and delivering electrical signals to a first electrode proximate to a left sympathetic nerve pathway and a second electrode proximate to a right sympathetic nerve pathway to stimulate sympathetic nerves and thereby increase cardiac output. A device for performing such an exemplary method. Such methods and/or device are optionally used in conjunction with sympathomimetic and/or sympatholytic agents.

The various apparatus and methods described herein, and equivalents thereof, are suitable for use in a variety of pacing therapies and other cardiac related therapies.

BRIEF DESCRIPTION OF THE DRAWINGS

Features and advantages of the described implementations can be more readily understood by reference to the following description taken in conjunction with the accompanying drawings.

FIG. 10 is a block diagram of an exemplary method for coordinated stimulation of sympathetic nerves, for example, left sympathetic nerves and/or right sympathetic nerves.

DETAILED DESCRIPTION

The following description is of the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators will be used to reference like parts or elements throughout.

Exemplary Stimulation Device

The techniques described below are intended to be implemented in connection with any stimulation device that is configured or configurable to stimulate nerves and/or stimulate and/or shock a patient's heart.

Figure 1:
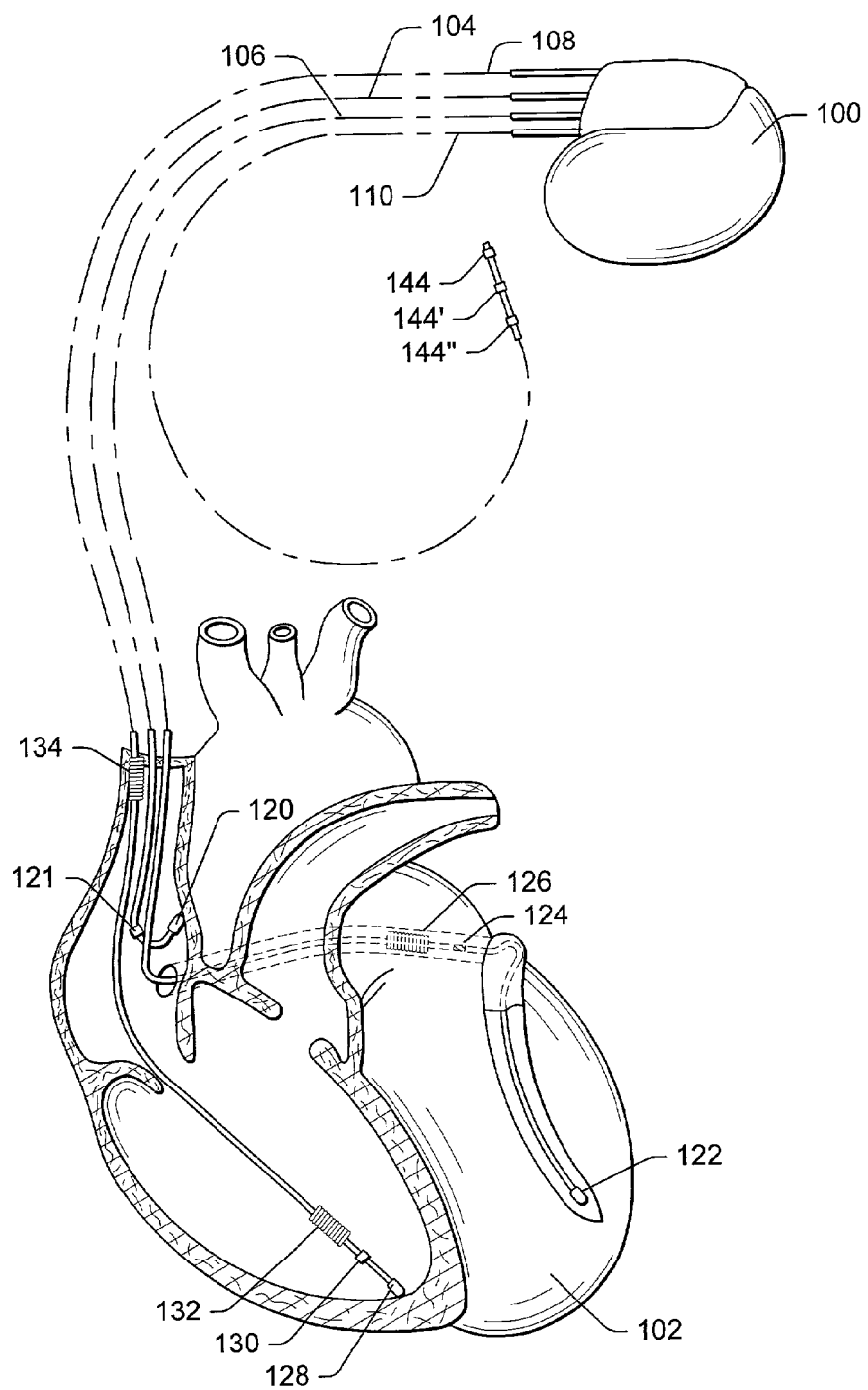
FIG. 1 is a simplified diagram illustrating an exemplary implantable stimulation device in electrical communication with at least three leads implanted into a patient's heart and at least one other lead for delivering stimulation and/or shock therapy.

FIG. 1 shows an exemplary stimulation device 100 in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of autonomic nerves. In addition, the device 100 includes a fourth lead 110 having, in this implementation, three electrodes 144, 144', 144" suitable for stimulation of autonomic nerves. This lead may be positioned in and/or near a patient's heart or near an autonomic nerve within a patient's body and remote from the heart. The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation of autonomic nerves.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. patent application Ser. No. 09/457,277, filed Dec. 8, 1999, entitled "A Self-Anchoring, Steerable Coronary Sinus Lead" (Pianca et. al); and U.S. Pat. No. 5,466,254, "Coronary Sinus Lead with Atrial Sensing Capability" (Helland), which are incorporated herein by reference. The coronary sinus lead 106 further optionally includes electrodes for stimulation of sympathetic nerves. Such a lead may include pacing and autonomic nerve stimulation functionality and may further include bifurcations or legs. For example, an exemplary coronary sinus lead includes pacing electrodes capable of delivering pacing pulses to a patient's left ventricle and at least one electrode capable of stimulating an autonomic nerve. An exemplary coronary sinus lead (or left ventricular lead or left atrial lead) may also include at least one electrode capable of stimulating an autonomic nerve, such an electrode may be positioned on the lead or a bifurcation or leg of the lead.

Stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating an autonomic nerve, such an electrode may be positioned on the lead or a bifurcation or leg of the lead.

Figure 2:
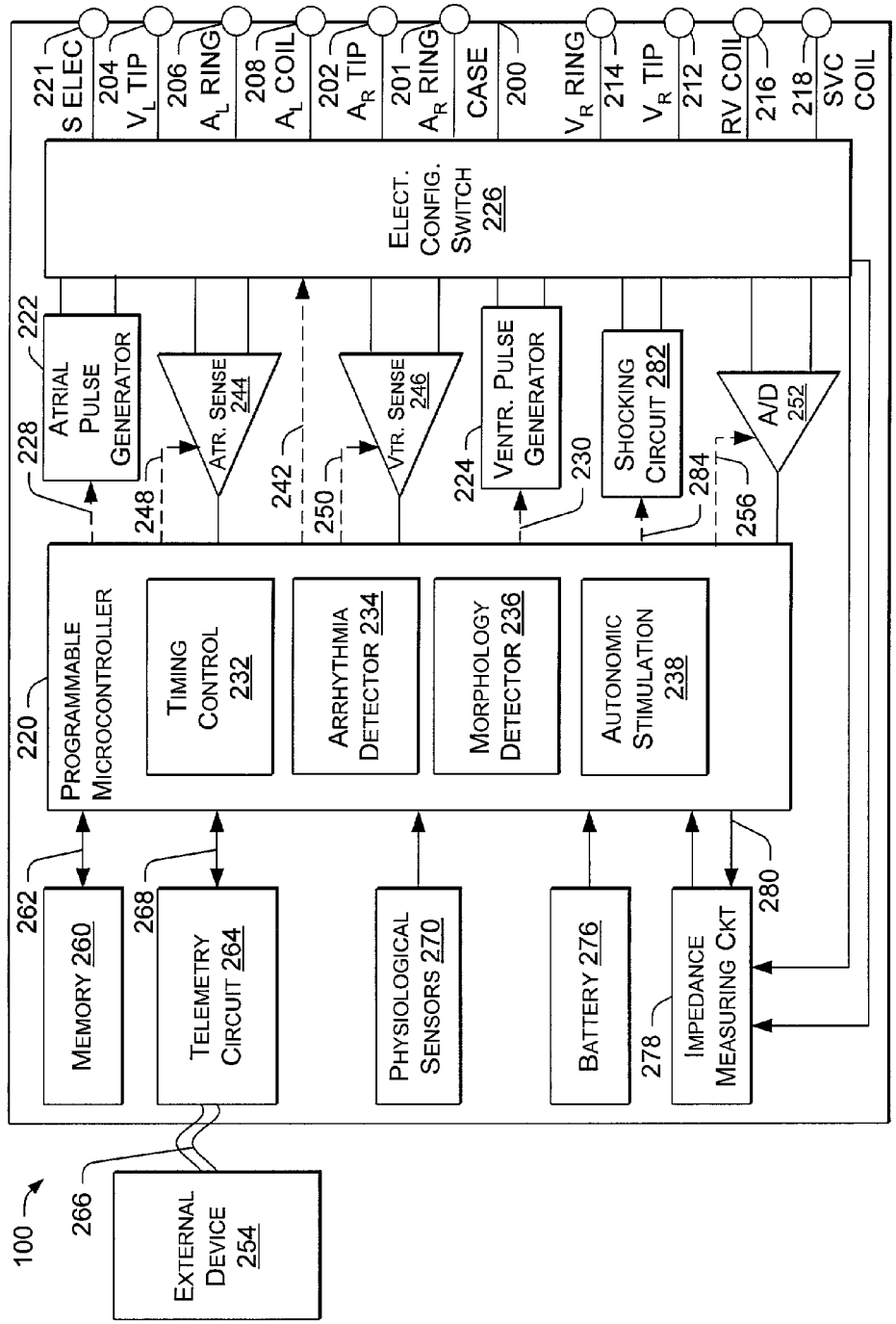
FIG. 2 is a functional block diagram of an exemplary implantable stimulation device illustrating basic elements that are configured to provide cardioversion, defibrillation, pacing stimulation and/or sympathetic nerve stimulation. The implantable stimulation device is further configured to sense information and administer stimulation pulses responsive to such information.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. The stimulation device can be solely or further capable of delivering stimuli to autonomic nerves. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, and/or autonomic nerve stimulation.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing, pacing and/or sympathetic stimulation, the connector includes at least a right atrial tip terminal (AR TIP) 202 adapted for connection to the atrial tip electrode 120. A right atrial ring terminal (AR RING) 201 is also shown, which is adapted for connection to the atrial ring electrode 121. To achieve left chamber sensing, pacing, shocking, and/or autonomic stimulation, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable autonomic nerve stimulation electrodes is also possible via these and/or other terminals (e.g., via a nerve stimulation terminal S ELEC 221).

To support right chamber sensing, pacing, shocking, and/or autonomic nerve stimulation, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively. Connection to suitable autonomic nerve stimulation electrodes is also possible via these and/or other terminals (e.g., via the nerve stimulation terminal S ELEC 221).

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. No. 4,712,555 (Sholder) and U.S. Pat. No. 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart (or to autonomic nerves) the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology detector 236, and optionally an orthostatic compensator and a minute ventilation (MV) response module, the latter two are not shown in FIG. 2. These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

Microcontroller 220 further includes an autonomic nerve stimulation module 238 for performing a variety of tasks related to autonomic nerve stimulation. This component can be utilized by the stimulation device 100 for determining desirable times to administer various therapies, including, but not limited to, sympathetic stimulation to, for example, increase contractility or rate of a patient's heart and/or parasympathetic stimulation to, for example, decrease rate of a patient's heart. The autonomic module 238 may be implemented in hardware as part of the microcontroller 220, or as software/firmware instructions programmed into the device and executed on the microcontroller 220 during certain modes of operation.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the nerve stimulation lead through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further include a physiologic sensor 270, commonly referred to as a "rate-responsive" sensor because it is typically used to adjust pacing stimulation rate according to the exercise state of the patient. However, the physiological sensor 270 may further be used to detect changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the microcontroller 220 responds by adjusting the various pacing parameters (such as rate, AV Delay, V—V Delay, etc.) at which the atrial and ventricular pulse generators, 222 and 224, generate stimulation pulses.

While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense respiration rate, pH of blood, ventricular gradient, cardiac output, preload, afterload, contractility, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 (Bornzin et. al), issued Dec. 19, 1995, which patent is hereby incorporated by reference.

More specifically, the physiological sensors 270 optionally include sensors for detecting movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 $\mu$A), and is capable of providing high-current pulses (for capacitor charging) when the patient requires a shock pulse (e.g., preferably, in excess of 2 A, at voltages above 2 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (up to 0.5 J), moderate (0.5 J to 10 J), or high energy (11 J to 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5 J to 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

Congestive Heart Failure (CHF)

Congestive heart failure (CHF) is a condition in which a weakened heart cannot pump enough blood to body organs. Heart failure may affect either the right side, left side, or both sides of the heart. As pumping action is lost, blood may back up into other areas of the body, including the liver, gastrointestinal tract, and extremities (right-sided heart failure), or the lungs (left-sided heart failure). Structural or functional causes of heart failure include high blood pressure (hypertension), valvular heart disease, congenital heart diseases, cardiomyopathy, heart tumor, and other heart diseases. Precipitating factors include infections with high fever or complicated infections, use of negative inotropic drugs (such as beta-blockers and calcium channel blocker), anemia, irregular heartbeats (arrhythmias), hyperthyroidism, and kidney disease.

The New York Heart Association has classified heart condition into four classes: Class I—patients with no limitation of activities; they suffer no symptoms from ordinary activities; Class II—patients with slight, mild limitation of activity; they are comfortable with rest or with mild exertion; Class III—patients with marked limitation of activity; they are comfortable only at rest; and Class IV—patients who should be at complete rest, confined to bed or chair; any physical activity brings on discomfort and symptoms occur at rest. Proper treatment of heart failure often relies on assessment of a patient's classification, see, e.g., Shamsham and Mitchell, "Essentials of the diagnosis of heart failure", *Am. Fam. Phys.*, Mar. 1, 2000 (pp. 1319–1330). For example, Shamsham and Mitchell present an algorithm for diastolic dysfunction and systolic dysfunction that references the NYHA classes.

One suggested treatment for CHF involves use of an angiotensin-converting enzyme (ACE) inhibitor, see, e.g., Cohn, "Preventing congestive heart failure", *Am. Fam. Phys.*, Apr. 15, 1998 (pp. 1901–1907). A number of potential mechanisms have been suggested to explain the efficacy of ACE inhibitors in preventing congestive heart failure. According to Cohn, the simplest explanation is that ACE inhibitors reduce vascular tone and, by lowering impedance, improve emptying of the left ventricle. Improved left ventricular systolic performance may reduce the risk of symptomatic heart failure. Cohn reported that another suggested mechanism involves progressive structural changes that occur in the left ventricular myocardium in patients who develop overt heart failure. In this mechanism, myocardial remodeling is characterized by an enlargement of the chamber and an increase in muscle mass. According to this mechanism, the chamber dilation is associated with a progressive reduction in wall motion, eventually resulting in a globally hypokinetic ventricle. ACE inhibitors have been demonstrated to inhibit remodeling associated with the progressive decline of ejection fraction and overt symptoms of heart failure in both animal and human studies. One disadvantage to ACE inhibitors is that they may result in hyperkalemia (elevated levels of potassium in the blood).

A variety of other treatments exist for patients with decompensated CHF, see, e.g., Loh, "Overview: Old and new controversies in the treatment of advanced congestive heart failure", *J. Card. Fail.*, 7(2 Suppl. 1): 1–7 (2001); and Gomberg-Maitland, et al., "Treatment of congestive heart failure", *Arch. Intern. Med.*, 161: 342–349 (2001). However, a need exists for new treatments such as the exemplary autonomic nerve stimulation and/or pacing therapies described below.

Autonomic Nervous System

The autonomic nervous system includes sympathetic and parasympathetic pathways. Both pathways include afferent pathways (e.g., from an organ to central neurons) and efferent pathways (e.g., postganglionic neurons from ganglia to an organ) that relate to functioning of the heart. For example, parasympathetic efferent postganglionic neurons, when stimulated, suppress atrial rate and contractile force, atrio-ventricular nodal conduction, and ventricular contractile force, also known as contractility or inotropy. Sympathetic efferent postganglionic neurons, when stimulated, generally increase heart rate and increase contractility. Note that contractility is associated with the term "inotropy", heart rate is associated with the term "chronotropy" and conduction velocity is associated with the term "dromotropy".

As already mentioned, stimulation of parasympathetic nerves acts to decrease heart rate while stimulation of sympathetic nerves acts to increase heart rate. Regarding sympathetic stimulation, norepinephrine is released by sympathetic nerves. After its release, norepinephrine acts on the sinoatrial node (SA node) to increase the rate of diastolic depolarization, and thereby increase heart rate, and acts on the atrioventricular node (AV node) to increase the velocity of conduction and diminish the refractory period during which the AV node is unresponsive to stimuli coming from the atrium.

Contractility (or inotropy) refers to the force or strength of cardiac muscle contractions. Stimulation of sympathetic nerves causes active contractility whereas Frank-Starling mechanism causes passive contractility. Active contractility involves norepinephrine, which increases myocardial calcium permeability (or conductance) and hence actin/myosin crossbridge interactions. Other mechanisms may also accompany the increase in calcium permeability.

In general, an increase in ventricular contractility causes an increase stroke volume, which, in turn, can increase cardiac output. Cardiac output (CO) depends on heart rate (HR) and stroke volume (SV) (e.g., CO equals HR times SV). Changes in ventricular contractility alter the rate of force and pressure development by the ventricle and therefore change the rate of ejection (i.e., ejection velocity). For example, an increase in contractility shifts the Frank-Starling curve, which causes a reduction in end-systolic volume and an increase in stroke volume. The increased stroke volume also causes a reduction in ventricular end-diastolic volume (i.e., preload). The end-systolic pressure-volume relationship (ESPVR) may define an inotropic state of the ventricle.

Changes in contractility also produce significant changes in ejection fraction (EF). Increasing contractility leads to an increase in EF, while decreasing contractility decreases EF. Therefore, EF is often used as a clinical index for evaluating the inotropic state of the heart. In heart failure, for example, an associated decrease in contractility leads to a fall in stroke volume as well as an increase in preload, thereby decreasing EF. The increased preload, if it results in a left ventricular end-diastolic pressure greater than approximately 20 mmHg, can lead to pulmonary congestion and edema. Treatment of a patient in heart failure with an inotropic drug (e.g., beta-adrenoceptor agonist or digoxin) shifts the depressed Frank-Starling curve up and to the left, thereby increasing stroke volume, decreasing preload, and increasing EF.

Changes in inotropic state are particularly important during exercise. Increases in inotropic state helps to maintain stroke volume at high heart rates. Increased heart rate alone decreases stroke volume because of reduced time for diastolic filling (decreased end-diastolic volume). When inotropic state increases at the same time, this decreases end-systolic volume to maintain stroke volume.

Figure 3:
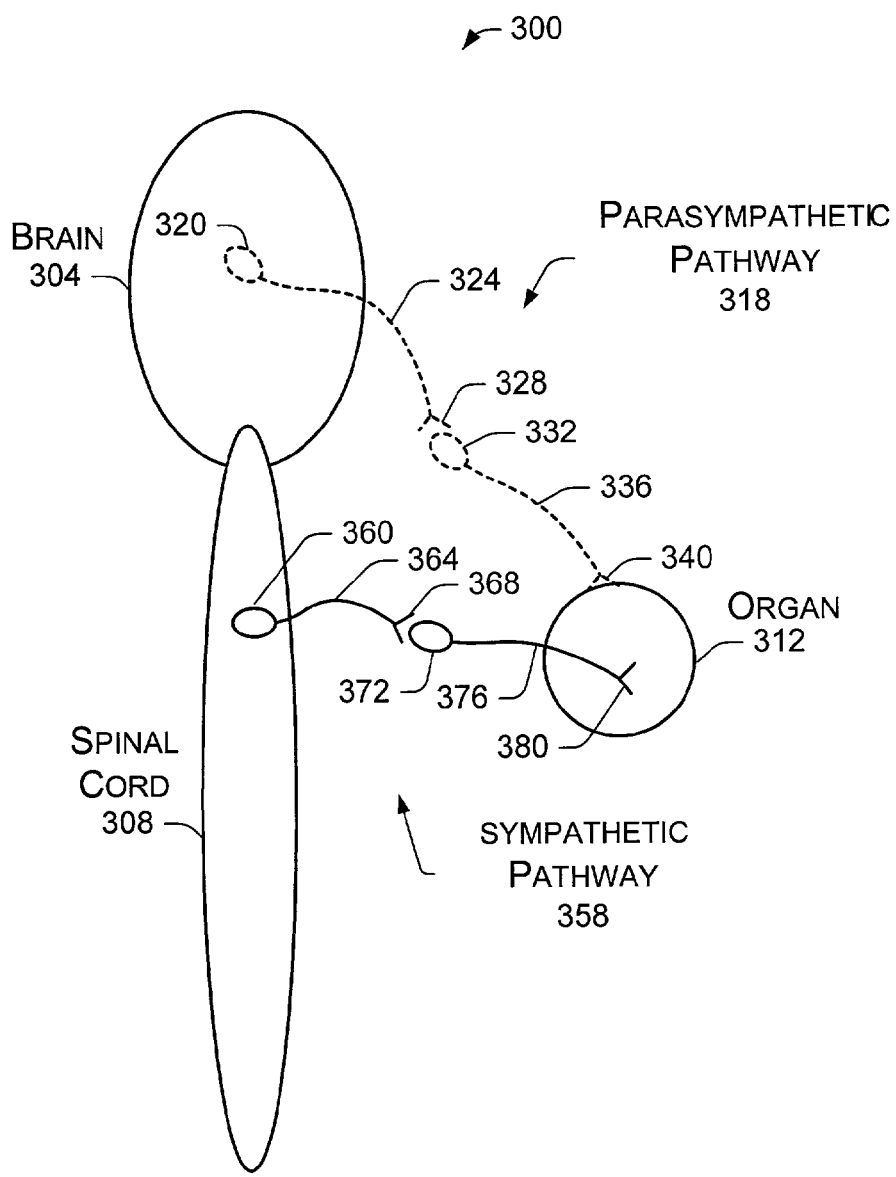
FIG. 3 is a simplified approximate anatomical diagram of a parasympathetic pathway and a sympathetic pathway of the autonomic nervous system.

As already mentioned, the autonomic nervous system includes parasympathetic and sympathetic pathways. Referring to FIG. 3, a simplified diagram of the autonomic nervous system 300 is shown. The system 300 illustrated includes a brain 304, a spinal cord 308, an organ 312, a parasympathetic efferent pathway 318 and a sympathetic efferent pathway 358. The parasympathetic efferent pathway 318 includes a preganglionic cell body 320 located in the brain 304, a preganglionic axon 324, a synaptic cleft 328, a postganglionic cell body 332, a postganglionic axon 336, and a postganglionic synaptic cleft 340 proximate to the organ 312. An exemplary parasympathetic stimulus originates at the brain 304 and ends at the postganglionic synaptic cleft 340 wherein a chemical is emitted to effect cell of the organ 312. A synaptic cleft may also be referred to as a neuroeffector junction. The sympathetic efferent pathway 358 includes a preganglionic cell body 360 located in the spinal cord 308, a preganglionic axon 364, a synaptic cleft 368, a postganglionic cell body 372, a postganglionic axon 376, and a postganglionic synaptic cleft 380 proximate to the organ 312. An exemplary sympathetic stimulus originates at the spinal cord 308 and ends at the postganglionic synaptic cleft 380 wherein a chemical is emitted to effect cell of the organ 312. In both pathways 318, 358, acetylcholine operates as a neurotransmitter to activate postganglionic neurons, i.e., preganglionic neurons are cholinergic. In parasympathetic pathways (e.g., the parasympathetic pathway 318), postganglionic neurons emit acetylcholine and are therefore cholinergic. However, in many sympathetic pathways (e.g., the sympathetic pathway 358), postganglionic neurons emit norepinephrine and are therefore adrenergic. While FIG. 3 shows a one to one ratio of preganglionic to postganglionic neurons, note that a preganglionic neuron generally links to more than one postganglionic neuron, for example, in a sympathetic pathway, a preganglionic neuron to postganglionic neuron ratio may be approximately 1:32. Sympathetic pathways having cardiac effect are described in more detail below.

Sympathetic Pathways

Figure 4:
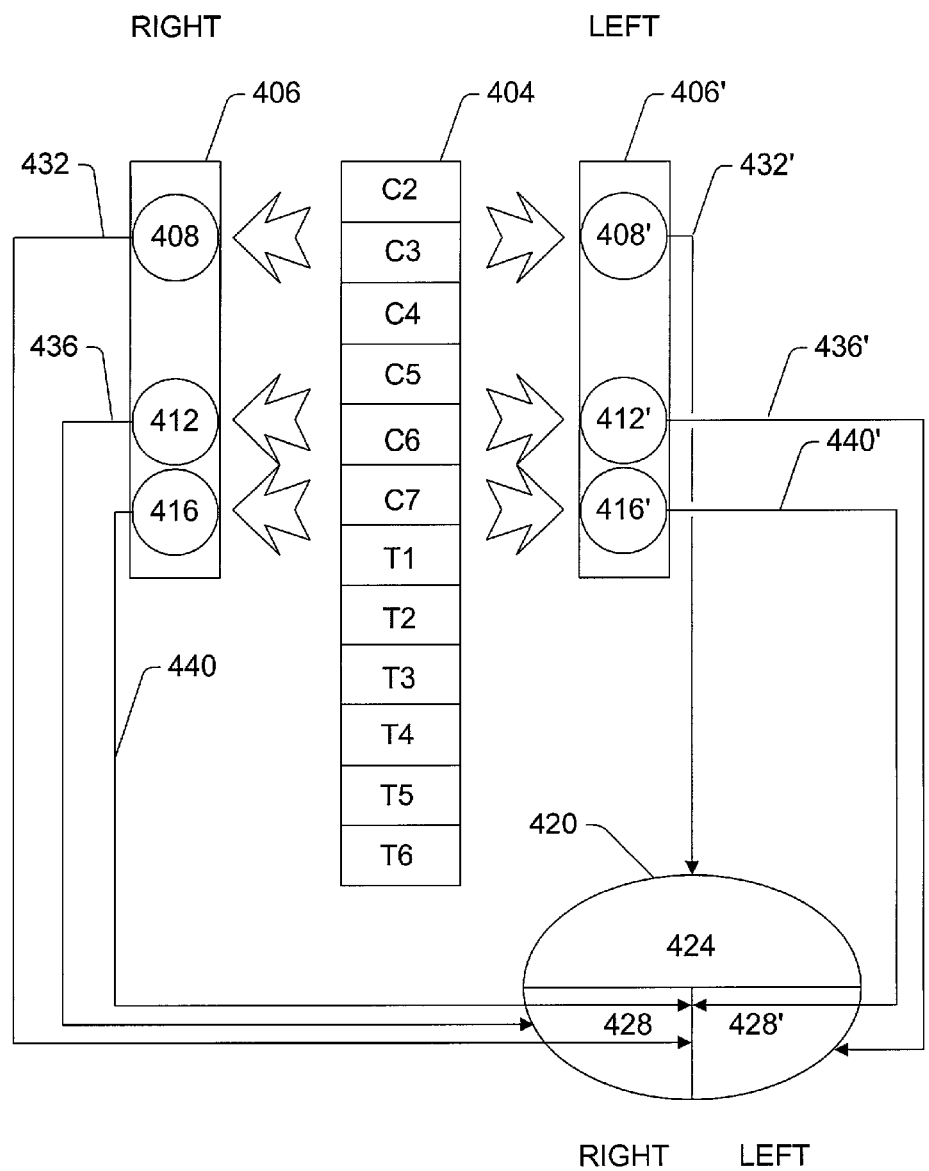
FIG. 4 is a simplified approximate anatomical diagram of sympathetic pathways to the heart.

Referring to FIG. 4, a block diagram of components of the sympathetic nervous system is shown. The sympathetic nervous system, which is not part of the central nervous system, includes two parallel chains or trunks, a right trunk 406 and a left trunk 406'. Each trunk includes a series of ganglia which lie just lateral to the spinal cord 404 on each side (left and right). In general, the uppermost region of each trunk (406, 406') has three cervical ganglia, which are continuous with the thoracic trunk. The cervical ganglia are known as the right and left superior cervical ganglia (408, 408'), the right and left middle cervical ganglia (412, 412') and the right and left inferior cervical ganglia (416, 416'), the latter of which are known as a stellate ganglion if they combine with a respective first thoracic ganglion. Stellate ganglia exist in approximately 70% to approximately 80% of the population.

Cardiac sympathetic fibers originate in intermediolateral columns of the upper five or six thoracic segments (see T1–T6 in FIG. 4) and lower one or two cervical segments (see C5 and C6 in FIG. 4) of the spinal cord 404. Sympathetic fibers enter the paravertebral chain and typically synapse in the cervical ganglia. Cardiac sympathetic ganglia are generally found close to the spinal column (paravertebral ganglia) and may stem from both thoracic and cervical preganglionic fibers. Postganglionic cardiac sympathetic nerves originate from the left and right ganglia and usually approach the base of the heart (e.g., as superior, middle, and inferior cardiac nerves) along the adventitial surface of the great vessels.

Each of the superior cardiac nerves 432, 432' arises by two or more branches from a respective superior cervical ganglion 408, 408', and occasionally receives a filament from the trunk between a first and/or a second cervical ganglia. The right superior cardiac nerve 432, at the root of the neck, passes either in front of or behind the subclavian artery, and along the innominate artery to the back of the arch of the aorta, where it joins the deep part 428, 428' of the epicardial plexus 420. The right superior cardiac nerve 432 connects with other sympathetic branches. About the middle of the neck the right superior cardiac nerve 432 receives filaments from the external laryngeal nerve; lower down, one or two twigs from the vagus; and as it enters the thorax it is joined by a filament from the recurrent nerve. In addition, filaments from the nerve communicate with the thyroid branches from the right middle cervical ganglion 412. The left superior cardiac nerve 432', in the thorax, runs in front of the left common carotid artery and across the left side of the arch of the aorta, to the superficial part 424 of the epicardial plexus 420.

Each of the middle cardiac nerves 436, 436' (or great cardiac nerves), the largest of the three cardiac nerves, arises from a respective middle cervical ganglion 412, 412', or from a respective trunk 406, 406' between the middle ganglion 412, 412' and the inferior ganglion 416, 416'. On the right side, the right middle cardiac nerve 436 descends behind the common carotid artery, and at the root of the neck runs either in front of or behind the subclavian artery; it then descends on the trachea, receives a few filaments from the recurrent nerve, and joins the right half of the deep part 428 of the epicardial plexus 420. In the neck, it communicates with the right superior cardiac nerve 432 and recurrent nerve. On the left side, the left middle cardiac nerve 436' enters the chest between the left carotid and subclavian arteries, and joins the left half of the deep part 428' of the epicardial plexus 420.

Each inferior cardiac nerve 440, 440' arises from the respective inferior cervical ganglion 416, 416' or the first thoracic ganglion (or stellate ganglion, e.g., 416, 416'). Both right and left inferior cardiac nerves 440, 440' descend behind the subclavian artery and along the front of the trachea, to join the deep part 428, 428' of the epicardial plexus 420. Each of the inferior cardiac nerves 440, 440' communicates freely behind the subclavian artery with the recurrent nerve and the respective middle cardiac nerve 436, 436'.

As already mentioned with reference to FIG. 4, at the base of the heart, the sympathetic fibers form an epicardial plexus 420 that distributes the fibers to the various regions of the heart. The epicardial plexus 420 has a superficial part 424 and a deep part (shown as a right deep part 428 and a left deep part 428' in FIG. 4), see, e.g., *Gray's anatomy: the anatomical basis of medicine and surgery*, 38th ed. (1995). The deep part 428, 428' lies upon the tracheal bifurcation (at the back of the aorta and in front of the tracheal bifurcation) and consists of cardiac branches from all cervical sympathetic ganglia of both right and left sides except the superior left 408', together with superior and inferior cervical and thoracic cardiac branches of the right vagus nerve (parasympathetic) and superior cervical and thoracic branches of the left vagus nerve (parasympathetic).

Pauza, et al., "Morphology, distribution, and variability of the epicardiac neural ganglionated subplexuses in the human heart", *The Anatomical Record* 259(4): 353–382 (2000), reported that the epicardial plexus forms seven subplexuses: (I) left coronary, (II) right coronary, (III) ventral right atrial, (IV) ventral left atrial, (V) left dorsal, (VI) middle dorsal, and (VII) dorsal right atrial. Pauza, et al., state that, in general, the human right atrium is innervated by two subplexuses (III, VII), the left atrium by three subplexuses (IV, V, VI), the right ventricle by one subplexus (II), and the left ventricle by three subplexuses (I, V, VI). Pauza, et al., also note that diagrams from Mizeres, "The cardiac plexus in man", *Am. J. Anat.* 112:141–151 (1963), suggest that "left epicardiac subplexuses may be considered as being formed by nerves derived from the left side of the deep extrinsic cardiac plexus, whereas ventral and dorsal right atrial subplexuses should be considered as being supplied by preganglionated nerves extending from the right vagus nerve and right sympathetic trunk, as their branches course in the adventitia of the right pulmonary artery and superior vena cava". Further, Pauza, et al., also state that the left coronary (I), right coronary (II), ventral left atrial (IV) and middle dorsal (VI) subplexuses "may be considered as being formed by the deep extrinsic plexus that receives equally from both vagi and sympathetic trunks". Note that in the Pauza, et al., reference, the terms "epicardiac preganglionated nerves" and "epicardiac postganglionated nerves" are differentiated from the meanings of "axons of the preganglionic and postganglionic neurons" that are valid in the nomenclature of the autonomic nervous system, for example, as referred to above with reference to FIG. 3 and FIG. 4. Thus, the term "postganglionic neurons" includes epicardiac/epicardial preganglionic neurons as well as epicardiac/epicardial postganglionic neurons.

Upon stimulation, end terminals (or terminal knobs) of the postganglionic sympathetic nerves (e.g., epicardial postganglionic sympathetic nerves) release norepinephrine, which acts upon the myocardium. Following stimulation and release, norepinephrine remains active for several seconds; norepinephrine may then be reabsorbed by the terminal, diffuse out of the area, or be inactivated by enzymes. The adrenal medulla also secretes norepinephrine (e.g., 75 percent epinephrine and 25 percent norepinephrine) and produces a peripheral effect that typically lasts much longer than that produced by stimulation of the sympathetic postganglionic terminal knobs. While circulating norepinephrine can increase contractility, the effect on normally innervated hearts is relatively minor with respect to norepinephrine released by end terminals. Heart rate, although initially stimulated by norepinephrine, usually decreases over time due to activation of baroreceptors and vagal-mediated (parasympathetic) slowing of the heart rate.

Cardiac tissue membrane receptors, such as alpha receptors and beta receptors, receive chemicals emitted by postganglionic nerves. Alpha receptors are the most common type of sympathetic receptor and they respond strongly to norepinephrine and weakly to epinephrine. Beta receptors are also adrenergic and include beta-1, beta-2 and beta-3 receptors. Cardiac sympathetic receptors are mostly the beta-1 subtype. Beta-1 receptors, which respond approximately equally to norepinephrine and epinephrine, generally act on the myocardium to increase heart rate, contractility, and/or conduction velocity. In contrast, parasympathetic cholinergic muscarinic receptors act on the sinoatrial (SA) node to decrease heart rate and act on the atrioventricular (AV) node to decrease conduction velocity. Adrenergic antagonists (indirect action) include beta-blockers such as proranolol and alpha-blockers such as phentolamine that inhibit receptors. Cholinergic antagonists (indirect action) include alpha-blockers such as atropine.

Electrical stimulation of autonomic nerves has been reported in the literature, see, e.g., Murakami, et al., "Effects of cardiac sympathetic nerve stimulation on the left ventricular end-systolic pressure-volume relationship and plasma norepinephrine dynamics in dogs", *Jpn. Circ. J.* 61(10): 864–71 (1997); and Du, et al., "Response to cardiac sympathetic activation in transgenic mice overexpressing beta 2-adrenergic receptor". *Am-J-Physiol.* August; 271(2 Pt 2): H630–6 (1996).

According to various exemplary methods and/or devices described herein, a series of pulses, or a pulse train, is typically delivered by an implantable stimulation device to stimulate an autonomic nerve. The pulse train optionally includes pulse parameters or pulse train parameters, such as, but not limited to, frequency, pulse duration (or pulse width), number of pulses, and/or amplitude. These parameters may have broad ranges and vary over time within any given pulse train. In general, a power level for individual pulses and/or pulse trains is determined based on these parameters and/or other parameters. Exemplary ranges for pulse frequency include frequencies ranging from approximately 0.1 to approximately 50 Hz, and, in particular, frequencies ranging from approximately 1 Hz to approximately 4 Hz. Of course, higher frequencies higher than 50 Hz may also be suitable. Exemplary ranges for pulse duration, or pulse width for an individual pulse (generally within a pulse train), include pulse widths ranging from approximately 0.01 milliseconds to approximately 5 milliseconds and, in particular, pulse widths ranging from approximately 0.1 milliseconds to approximately 1.6 milliseconds. Exemplary pulse amplitudes are typically given in terms of current or voltage; however, a pulse or a pulse trains may also be specified by power, charge and/or energy. For example, in terms of current, exemplary ranges for pulse amplitude include amplitudes ranging from approximately 0.02 mA to approximately 20 mA, in particular, ranging from 0.1 mA to approximately 5 mA. Exemplary ranges for pulse amplitude in terms of voltage include voltages ranging from approximately 2 V to approximately 50 V, in particular, ranging from approximately 4 V to approximately 15 V.

For pulses delivered by implantable stimulation devices having a fixed or otherwise limited power supply, i.e., a power supply having power limitations, average power of a pulse or a pulse train is usually limited acutely by the power capability of the power supply (e.g., battery, fuel cell, nuclear generator, etc.) and chronically by the capacity of the power supply and desired longevity of the device's usefulness. Average power of a pulse is generally given as peak power averaged over one cycle. For example, given a voltage of 10 V, a resistance of 1000 ohms, a pulse frequency of 20 Hz and a pulse width of 1 ms, the peak power is given as voltage squared divided by resistance, which is 0.1 W, and the average power is 20 Hz multiplied by 1 ms multiplied by 0.1 W, which is 0.002 W or 2 mW. The term "power", as used herein, includes, but is not limited to, peak power and average power.

Current drain is another factor often considered when determining power limitations of a power supply. Current drain is generally defined as the average amount of current drawn from a power supply in an implantable pulse generator in one hour. Current drain depends on many factors, including how frequently the device delivers pulses and at what parameters, the circuitry and/or the type of stimulation lead. Current drain is commonly expressed in millionths of an ampere or microamperes. A power drain based on current drain may be determined by the product of current drain and voltage. Such a power is optionally useful in determining a maximum power level for an autonomic stimulation pulse or pulses.

In general, a maximum power level or maximum power demand for an implantable device may be determined, in part, by the product of the voltage times the current capability of the battery (or other power supply) less circuit inefficiencies. Of course, desired power supply life (e.g., battery life) and/or other factors may be considered. For example, some implantable stimulation devices have a continuous power drain for one function (e.g., to drive a microchip, microprocessor or timing circuitry) and an intermittent function (e.g., such as pacing, measuring, signaling, etc.) which has intermittent power utilization. Consideration of such factors may be necessary in determining a tolerable and/or maximum power level and, in particular, in determining pulse parameters for autonomic nerve stimulation.

Epicardial Sympathetic Pathways

According to various exemplary methods and stimulation devices described herein, and equivalents thereof, stimulation of sympathetic nerves allows for influence of cardiac activity, and, in particular, stimulation of epicardial sympathetic nerves. For example, various exemplary methods and corresponding stimulation devices rely on placement of an electrode in an epicardial vein or an epicardial venous structure. Suitable epicardial veins or venous structures include the coronary sinus and veins that drain into the coronary sinus, either directly or indirectly. For example, the great cardiac vein passes along the interventricular sulcus, with the anterior interventricular coronary artery, and empties anteriorly into the coronary sinus; and the middle cardiac vein travels with the posterior (right) interventricular coronary artery and empties into the coronary sinus posteriorly. Other suitable veins include those that drain into the right atrium or right auricle. For example, the anterior cardiac vein passes through the wall of the right atrium and empties into the right atrium.

Figure 5:
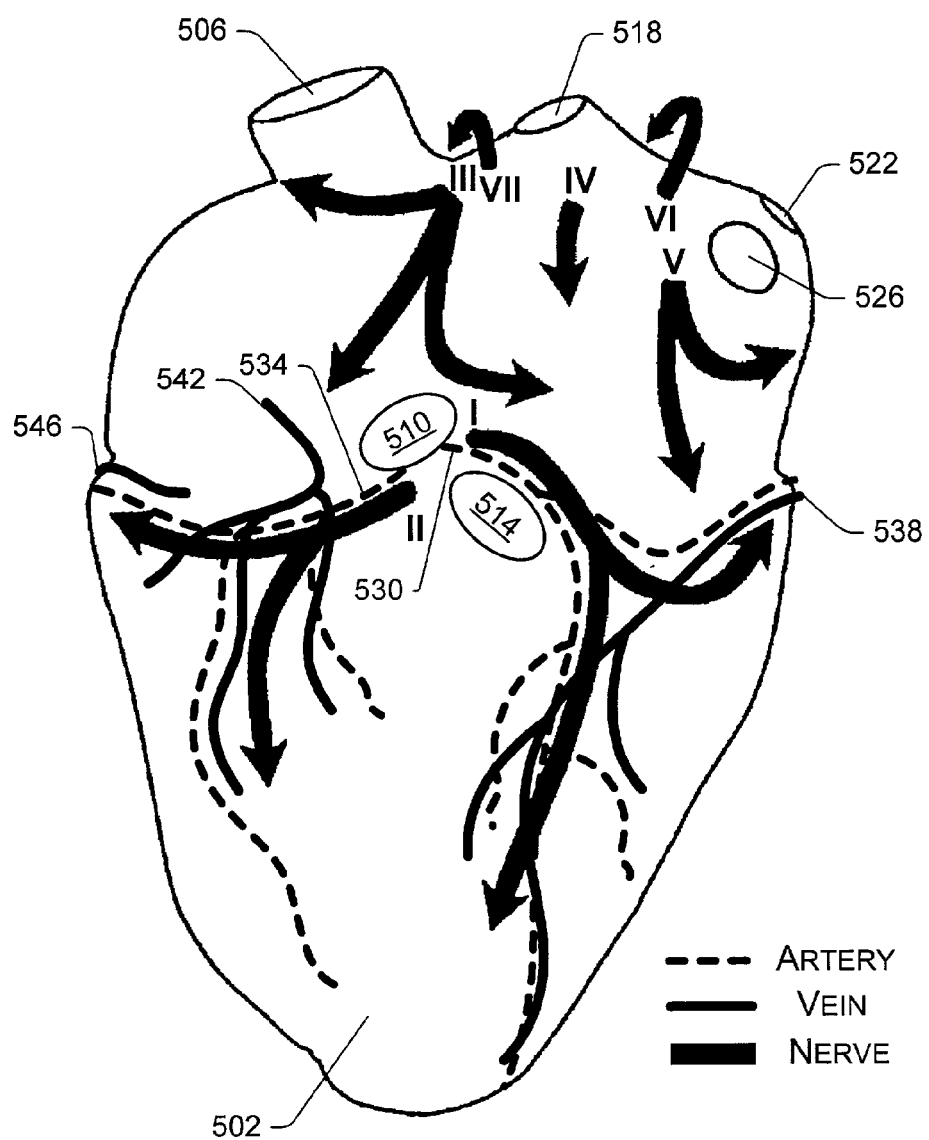
FIG. 5 is an approximate anatomical ventral view diagram of a human heart including some arteries, veins and nerves.

Referring to FIG. 5, a ventral diagram of a human heart 502 is shown. Various anatomical features of the heart 502 are also shown and include an opening to the superior vena cava 506, an opening to the aorta 510, an opening to the pulmonary trunk 514, an opening to the right superior pulmonary vein 518, an opening to the left inferior pulmonary vein 522, and an opening to the left superior pulmonary vein 526. FIG. 5 also shows some of the epicardial arteries (thick dashed lines) and veins (thick solid lines). Under normal conditions, epicardial arteries carry oxygenated blood to the myocardium, primarily myocardium of the ventricles while epicardial veins carry blood deoxygenated by the myocardium to the right atrium of heart 502. Pressure in the veins is generally, on average, much less than pressure in the arteries.

Two major epicardial arterial networks are shown in FIG. 5 and associated with the left coronary artery 530 and the right coronary artery 534. The left coronary artery 530 stems from the aorta near the opening to the aorta 510 and travels along the base of the left ventricle where it branches. One branch of the left coronary artery travels on the epicardial surface of the left ventricle toward the apex of the heart 502 (known as the left anterior descending artery) while another branch travels on the epicardial surface of the left ventricle toward the dorsal side of the heart 502 (known as the circumflex branch of the left coronary artery). The right coronary artery 534 stems from the aorta near the opening to the aorta 510 and travels along the base of the right ventricle where it branches. Various branches of the right coronary artery 534 travel on the epicardial surface of the right ventricle while at least one branch travels on the epicardial surface of the right ventricle toward the dorsal side of the heart 502.

Three major epicardial venous networks are shown in FIG. 5, which are associated with the great cardiac vein 538, the anterior cardiac vein 542, and the small cardiac vein 546. The great cardiac vein 538 receives blood from a network that spreads across the ventral side of the epicardial surface of the left ventricle and major branches of the network extend toward the apex of the heart 502. As already mentioned, the great cardiac vein 538 travels on the epicardial surface near the base of the left ventricle to the dorsal side of the heart 502 where it joins the coronary sinus vein. The anterior cardiac vein 542 receives blood from a network that spreads across the ventral and dorsal sides of the epicardial surface of the right ventricle and major branches of the network extend toward the apex of the heart 502. As already mentioned, the anterior cardiac vein empties into the right atrium of the heart 502. The small cardiac vein 546 travels from the ventral epicardial surface to the dorsal epicardial surface where it empties into the coronary sinus.

FIG. 5 also shows the seven subplexuses as identified by Pauza, et al. Preganglionate nerves enter the left coronary subplexus (I) and the right coronary subplexus (II) approximately between the opening to the aorta 510 and the opening to the pulmonary trunk 514. Preganglionate nerves enter the ventral right atrial subplexus (III) at the superior interatrial sulcus and non-regularly on the ventral surface of the root of the superior vena cava while preganglionated nerves enter the ventral left atrial subplexus (IV) approximately between the superior interatrial sulcus and left atrial nerve fold. Preganglionated nerves enter the left dorsal subplexus (V) approximately at the left atrial nerve fold and preganglionated nerves enter the middle dorsal subplexus (VI) approximately between the right and left superior pulmonary veins (see, e.g., 518, 526) and, non-regularly, between the right pulmonary veins and the inferior vena cava. Preganglionated nerves enter the dorsal right atrial subplexus (VII) approximately between the superior vena cava and the right superior pulmonary vein (see, e.g., 506, 518). As already mentioned, postganglionated nerves, and some preganglionated nerves, spread out from the subplexuses (I–VII) across the epicardial surface of the heart 502. The spreading of such nerves is shown by the thick solid arrows in FIG. 5 and FIG. 6, the latter of which shows a dorsal diagram of the heart 502.

Figure 6:
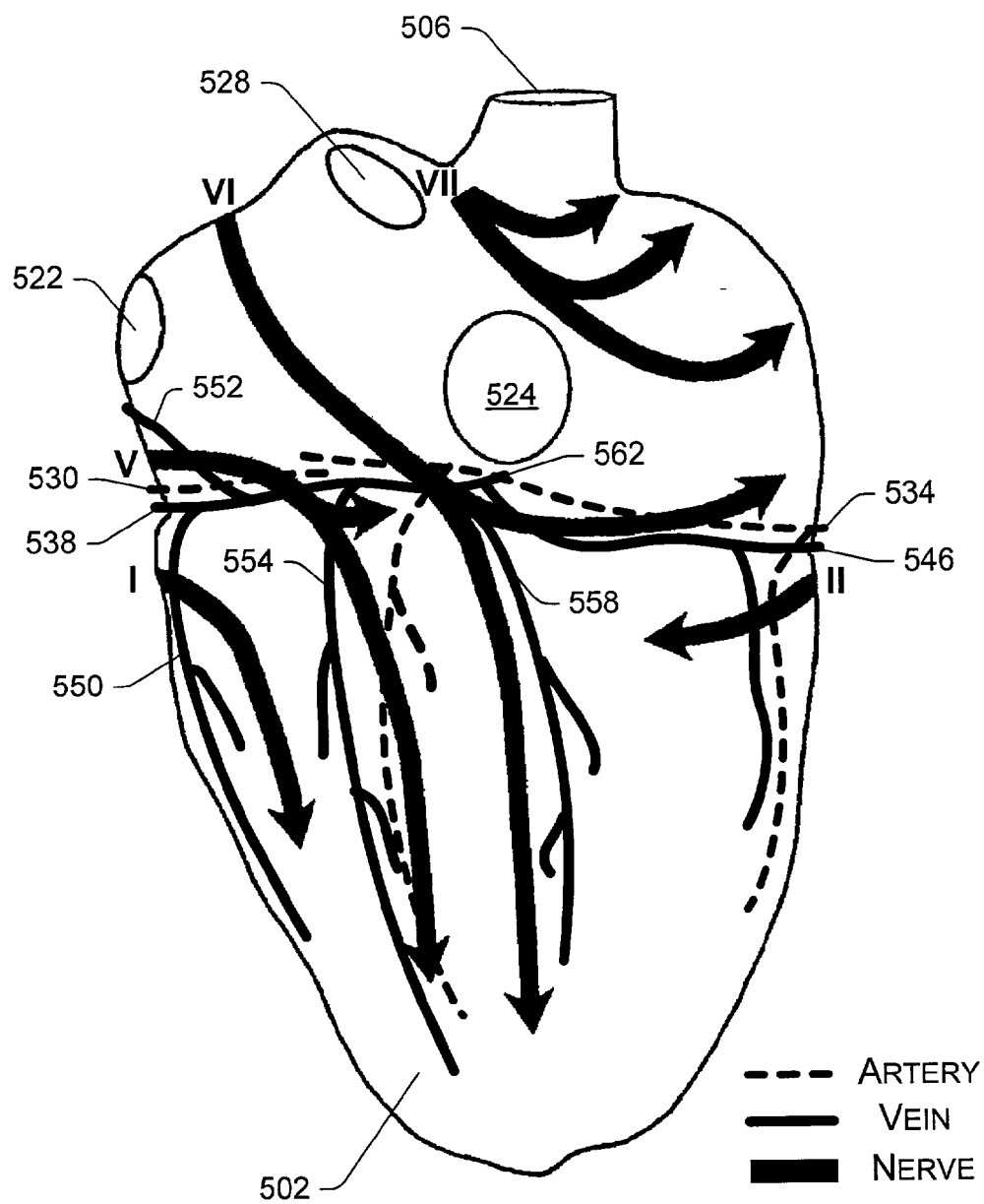
FIG. 6 is an approximate anatomical dorsal view diagram of a human heart including some arteries, veins and nerves.

Referring to FIG. 6, a dorsal diagram of the human heart 502 is shown. Various anatomical features of the heart 502 are also shown and include an opening to the superior vena cava 506, an opening to the inferior vena cava 524, an opening to the right inferior pulmonary vein 528, and an opening to the left inferior pulmonary vein 522. FIG. 6 also shows some of the epicardial arteries (thick dashed lines) and veins (thick solid lines). The arterial and venous networks shown on the dorsal epicardial surface of the heart 502 include extensions of networks from the ventral epicardial surface. For example, the dorsal epicardial surface includes networks stemming the right coronary artery 534 and the left coronary artery 530. In particular, the circumflex branch of the left coronary artery 530 is shown along with various extensions of the right coronary artery 534 one of which approaches the end of the circumflex branch. Venous epicardial structures shown in FIG. 6 include the coronary sinus 562, the great cardiac vein 538, the small cardiac vein 546, the oblique vein of the left atrium 552, the left marginal vein 550, the posterior vein of the left ventricle 554, and the middle cardiac vein 558. The aforementioned veins (538, 546, 550, 552, 554, 558) empty into the coronary sinus 562.

FIG. 6 also shows, via thick solid arrows, neural extensions of five of the subplexuses as identified by Pauza, et al. Neural extensions of the left coronary subplexus (I) descend toward the apex of the heart 502 at and/or near the left marginal vein 550 and the posterior vein of the left ventricle 554. Neural extensions of the right coronary subplexus (II) traverse the heart 502 at and/or near the right coronary sulcus. Neural extensions of the left dorsal subplexus (V) descend toward the apex of the heart 502 at and/or near the posterior vein of the left ventricle 554 while neural extensions of the middle dorsal subplexus (VI) descend towards the apex of the heart 502 at and/or near the middle cardiac vein 558 and the small cardiac vein 546. Neural extensions of the dorsal right atrial subplexus (VII) extend around the right atrium at and/or near the superior vena cava (see, e.g., 506) and the inferior vena cava (see, e.g., 524).

As shown in FIGS. 5 and 6, various epicardial veins or venous structures travel at and/or near epicardial subplexuses and/or epicardial extensions of epicardial subplexuses. According to various exemplary methods and/or stimulation devices described herein, at least one electrode is placed in the lumen of an epicardial vein or venous structure. Further, upon passing current through the at least one electrode, neural stimulation occurs, which preferably causes release of a neuroeffector, such as, but not limited to, norepinephrine.

Right Sympathetic Pathway Stimulation

Figure 7:
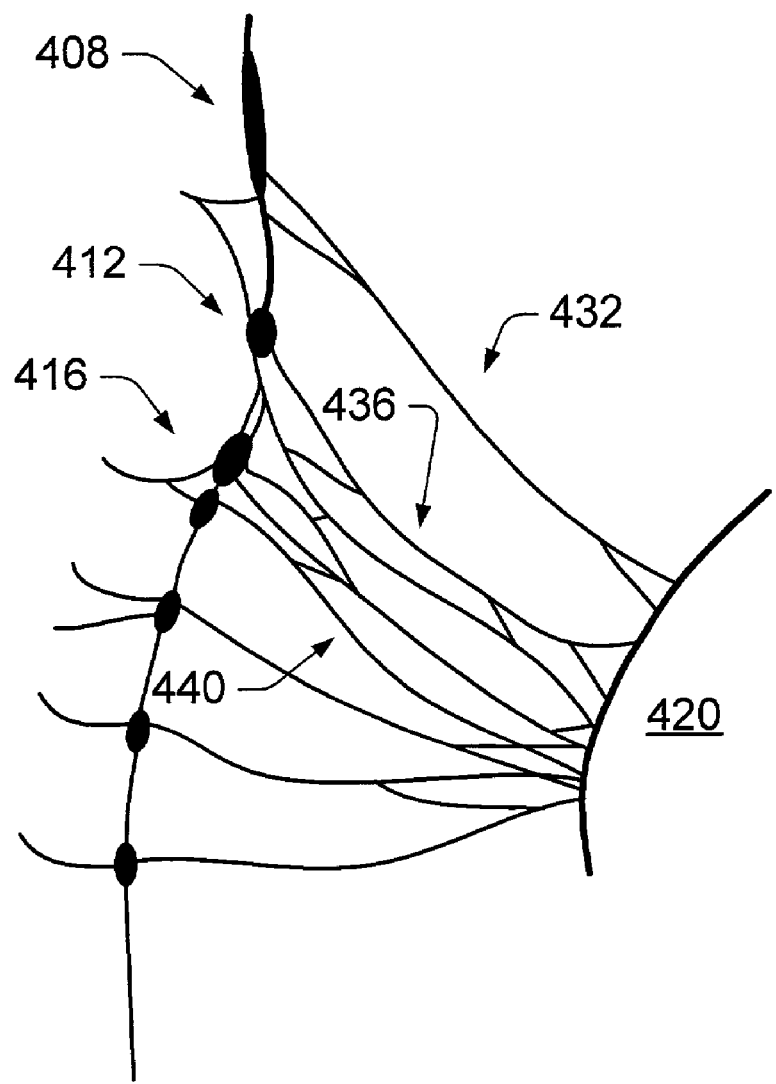
FIG. 7 is an approximate anatomical diagram of sympathetic pathways to the heart.

Referring again to FIG. 4, right sympathetic pathways are shown. The right cervical ganglia include the right superior cervical ganglion 408, the right middle cervical ganglion 412 and the right inferior cervical ganglion 416, the latter of which is known as the right stellate ganglion if it combines with the right first thoracic ganglion. As described herein, the ganglion labeled 416 represents the right inferior cervical ganglion, the right stellate ganglion and/or the right first thoracic ganglion. A generalized approximate anatomical diagram of right side or left side sympathetic pathways appears in FIG. 7; however, note that differences exist between right and left pathways, which are not shown in FIG. 7. FIG. 7 shows a variety of ganglia (e.g., 408, 412, 416) and nerves (e.g., 432, 436, 440) that innervate the cardiac plexus (e.g., 420).

In general, stimulation of right sympathetic nerves causes a pronounced increase in heart rate and a lesser increase in inotropy whereas stimulation of left sympathetic nerves causes a lesser increase in heart rate and a pronounced increase in inotropy, see, e.g., Miyano, et al., "Dynamic sympathetic regulation of left ventricular contractility studied in the isolated canine heart", Am. J. Physiol., 275: H400–H408 (1998); Armour, "Myocardial ischaemia and the cardiac nervous system," Cardiovascular Research, 41: 41–54 (1999); and Kralios, et al., "Local ventricular repolarization changes due to sympathetic nerve-branch stimulation", American J. Physiology, 228(5):1621–1626 (1975). According to Armour, stimulation of right sympathetic nerves (e.g., stemming from the right sympathetic trunk 406) typically yields a pronounced effect on heart rate and according to Kralios, et al., "right-stellate cardiac nerve stimulation always resulted in marked sinus tachycardia". Kralios, et al., further reported that "sympathetic fibers on the right side which alter recovery properties of the ventricular myocardium are distributed mostly via the recurrent cardiac nerve".

Right Superior Cervical Ganglion and Right Superior Cardiac Nerve

As shown in FIG. 4, the right superior cardiac nerve 432 arises by two or more branches from the right superior cervical ganglion 408, and occasionally receives a filament from the right trunk 406 between a first and/or a second cervical ganglia. The right superior cardiac nerve 432, at the root of the neck, passes either in front of or behind the subclavian artery, and along the innominate artery to the back of the arch of the aorta, where it joins the deep part (e.g., 428 and/or 428') of the epicardial plexus 420.

Stimulation of the right superior cervical ganglion 408 and/or the right superior cardiac nerve 432 is highly likely to cause stimulation of additional sympathetic branches and/or parasympathetic branches. For example, about the middle of the neck the right superior cardiac nerve 432 receives filaments from the external laryngeal nerve; lower down, one or two twigs from the vagus; and as it enters the thorax it is joined by a filament from the recurrent nerve (which branches from the vagus and surrounds the arterial duct). In addition, filaments from the nerve communicate with the thyroid branches from the right middle cervical ganglion 412. Thus, stimulation of the right superior cervical ganglion 408 and/or the right superior cardiac nerve 432 may also cause stimulation of the right middle cardiac nerve 436 and/or parasympathetic nerves (e.g., vagus nerve, recurrent nerve). Ultimately, supra-threshold stimulation of the right superior cervical ganglion 408 and/or the right superior cardiac nerve 432 will cause activation of nerves in the deep part 428, 428' of the epicardial plexus 420. Of course, electrodes may be positioned to minimize and/or eliminate stimulation of certain nerves (e.g., parasympathetic, left sympathetic, etc.).

Right Middle Cervical Ganglion and Right Middle Cardiac Nerve

The right middle cardiac nerve 436 (or right great cardiac nerve), arises from the right middle cervical ganglion 412, or from the right trunk 406 between the right middle ganglion 412 and the right inferior ganglion 416 (see, e.g., FIG. 7). The right middle cardiac nerve 436 descends behind the common carotid artery, and at the root of the neck runs either in front of or behind the subclavian artery; it then descends on the trachea, receives a few filaments from the recurrent nerve, and joins the right half of the deep part 428 of the epicardial plexus 420. In the neck, it communicates with the right superior cardiac nerve 432 and recurrent nerve. Thus, supra-threshold stimulation of the right middle cervical ganglion 412 and/or the middle cardiac nerve 436 may also cause stimulation of the right superior cardiac nerve 408 and/or the recurrent nerve. Ultimately, supra-threshold stimulation of the right middle cervical ganglion 412 and/or the right middle cardiac nerve 436 will cause activation of nerves in the right half of the deep part 428 of the epicardial plexus 420. Of course, electrodes may be positioned to minimize and/or eliminate stimulation of certain nerves (e.g., parasympathetic, left sympathetic, etc.).

Right Inferior Cervical Ganglion and Right Inferior Cardiac Nerve

The right inferior cardiac nerve 440 arises from the right inferior cervical ganglion 416 or the first thoracic ganglion (or the right stellate ganglion 416). The right inferior cardiac nerve 440 descends behind the subclavian artery and along the front of the trachea, to join the deep part 428, 428' of the epicardial plexus 420. The right inferior cardiac nerve 440 communicates freely behind the subclavian artery with the recurrent nerve and the right middle cardiac nerve 436.

Thus, supra-threshold stimulation of the right inferior cervical ganglion 416 (or right stellate ganglion or right first thoracic ganglion) and/or the right inferior cardiac nerve 440 may also cause stimulation of the right middle cardiac nerve 412 and/or the recurrent nerve. Ultimately, supra-threshold stimulation of the right inferior cervical ganglion 416 (or right stellate ganglion or right first thoracic ganglion) and/or the right inferior cardiac nerve 440 will cause activation of nerves in the deep part 428, 428' of the epicardial plexus 420. Of course, electrodes may be positioned to minimize and/or eliminate stimulation of certain nerves (e.g., parasympathetic, left sympathetic, etc.).

Epicardial Right Sympathetic Pathways

As already mentioned, the ventral and dorsal right epicardial subplexuses (labeled II and VII, respectively in FIGS. 5 and 6), can be considered as being supplied by nerves of the right sympathetic pathways. Thus, according to various exemplary methods and/or devices described herein, direct stimulation of these epicardial subplexuses, and/or nerves extending from these subplexuses, will cause an increase in heart rate.

Exemplary Method for Increasing Heart Rate

Figure 8:
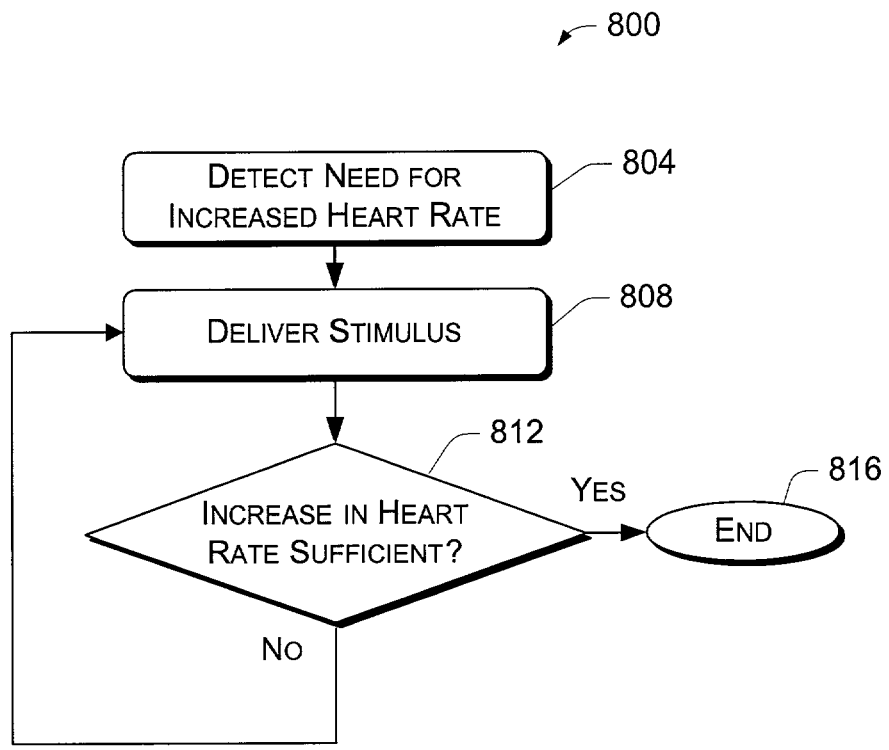
FIG. 8 is a block diagram of an exemplary method for stimulating right sympathetic nerves to increase heart rate.

FIG. 8 shows a block diagram of an exemplary method for stimulating sympathetic nerves 800 to increase heart rate. In a detection block 804, a stimulation or other device determines a need for increased heart rate. If a need exists, then, in a delivery block 808, a stimulation device delivers a stimulus to a sympathetic nerve associated with the right sympathetic trunk. The stimulus may be delivered via an electrode positioned in a vein, especially an epicardial vein, and/or in the pericardium using one or a variety of stimulation pulses. Optionally the electrodes may be placed directly epicardially during open chest surgery or through minimally invasive laproscopic procedures. The stimulation device optionally delivers the pulses during a refractory period (e.g., determined by the device, etc.) to avoid direct electrical stimulation of the myocardium. In a post-stimulation block 812, the stimulation or other device determines whether and/or to what extent heart rate has increased. If the increase is sufficient, then the method 800 terminates in an end block 816. If the increase is insufficient, then the method 800 returns to the delivery block 808. The device is further optionally programmable to make attempts at increasing and/or decreasing the pulse frequency, pulse width, pulse amplitude, and/or other parameters. The method 800 optionally includes a wait block between the delivery block 808 and the post-stimulation block 812 and/or between the post-stimulation block 812 and the return to the delivery block 808, in the case that the effect of the stimulation is insufficient. The exemplary method 800 may also account for other cardiac functions.

Left Sympathetic Pathway Stimulation

Referring again to FIG. 4, left sympathetic pathways are shown. The left cervical ganglia include the left superior cervical ganglion 408', the left middle cervical ganglion 412' and the left inferior cervical ganglion 416', the latter of which is known as the left stellate ganglion if it combines with the left first thoracic ganglion. As described herein, the ganglion labeled 416' represents the left inferior cervical ganglion, the left stellate ganglion and/or the left first thoracic ganglion. A generalized approximate anatomical diagram of right side or left side sympathetic pathways appears in FIG. 7; however, note that differences exist between right and left pathways, which are not shown in FIG. 7. FIG. 7 shows a variety of ganglia (e.g., 408, 412, 416) and nerves (e.g., 432, 436, 440) that innervate the cardiac plexus (e.g., 420).

In general, stimulation of right sympathetic nerves causes a pronounced increase in heart rate and a lesser increase in inotropy whereas stimulation of left sympathetic nerves causes a lesser increase in heart rate and a pronounced increase in inotropy, see, e.g., Miyano, et al., "Dynamic sympathetic regulation of left ventricular contractility studied in the isolated canine heart", *Am. J. Physiol.*, 275: H400–H408 (1998); Armour, "Myocardial ischaemia and the cardiac nervous system," *Cardiovascular Research*, 41: 41–54 (1999); and Kralios, et al., "Local ventricular repolarization changes due to sympathetic nerve-branch stimulation", *American J. Physiology*, 228(5):1621–1626 (1975). According to Armour, stimulation of left sympathetic nerves (e.g., stemming from the left sympathetic trunk 406') typically yields a pronounced effect on contractility and according to Kralios, et al., left-stellate cardiac nerve stimulation "caused atrioventricular junctional tachycardia, but no changes in electrocardiographic waveform". In addition, stimulation of the left ventrolateral nerve resulted in significant and more pronounced shortening of refractory periods than stimulation of stellate cardiac nerves. Kralios, et al., further reported that "on the left side, sympathetic fibers that innervate the ventricular myocardium are distributed via the ventrolateral cardiac nerve and to a lesser extent via the ventromedial nerve" wherein little overlap exists between the recurrent cardiac ventrolateral nerves.

Left Superior Cervical Ganglion and Left Superior Cardiac Nerve

The left superior cardiac nerve 432' arises by two or more branches from the left superior cervical ganglion 408', and occasionally receives a filament from the trunk between a first and/or a second cervical ganglia. The left superior cardiac nerve 408', in the thorax, runs in front of the left common carotid artery and across the left side of the arch of the aorta, to the superficial part 424 of the epicardial plexus 420. Thus, supra-threshold stimulation of the left superior cervical ganglion 408' and/or the left superior cardiac nerve 432' will cause activation of nerves in the superficial part 424 of the epicardial plexus 420. Of course, electrodes may be positioned to minimize and/or eliminate stimulation of certain nerves (e.g., parasympathetic, right sympathetic, etc.).

Left Middle Cervical Ganglion and Left Middle Cardiac Nerve

The left middle cardiac nerve 436' (or left great cardiac nerve), the largest of the three cardiac nerves, arises from the left middle cervical ganglion 412', or from the left trunk 406' between the left middle ganglion 412' and the left inferior ganglion 416'. On the left side, the left middle cardiac nerve 436' enters the chest between the left carotid and subclavian arteries, and joins the left half of the deep part 428' of the epicardial plexus 420. Thus, supra-threshold stimulation of the left middle cervical ganglion 412' and/or the left superior cardiac nerve 436' will cause activation of nerves in the left half of the deep part 428' of the epicardial plexus 420. Of course, electrodes may be positioned to minimize and/or eliminate stimulation of certain nerves (e.g., parasympathetic, right sympathetic, etc.).

Left Inferior Cervical Ganglion and Left Inferior Cardiac Nerve

The left inferior cardiac nerve 440' arises from the left inferior cervical ganglion 416' or the left first thoracic ganglion (or left stellate ganglion, e.g., 416'). The left inferior cardiac nerve 440' descends behind the subclavian artery and along the front of the trachea, to join the deep part 428, 428' of the epicardial plexus 420. The left inferior cardiac nerve 440' communicates freely behind the subclavian artery with the recurrent nerve and the left middle cardiac nerve 436'. Thus, supra-threshold stimulation of the left inferior cervical ganglion 416' (or left stellate ganglion or left first thoracic ganglion) and/or the left inferior cardiac nerve 440' may also cause stimulation of the left middle cardiac nerve 412' and/or the recurrent nerve. Ultimately, supra-threshold stimulation of the left inferior cervical ganglion 416' (or left stellate ganglion or left first thoracic ganglion) and/or the left inferior cardiac nerve 440' will cause activation of nerves in the deep part 428, 428' of the epicardial plexus 420. Of course, electrodes may be positioned to minimize and/or eliminate stimulation of certain nerves (e.g., parasympathetic, right sympathetic, etc.).

Epicardial Left Sympathetic Pathways

As already mentioned, the left coronary subplexus (I), the ventral left atrial subplexus (IV), the left dorsal subplexus (V) and the middle dorsal subplexus (VI) (as shown in FIGS. 5 and 6), should be considered as being supplied by nerves of the left side of the deep part 428' of the epicardial plexus and hence, in significant part, by at nerves from the left middle cervical ganglion 412' and the inferior left cervical ganglion 416' (e.g., left stellate ganglion or left first thoracic ganglion). Thus, according to various exemplary methods and/or devices described herein, direct stimulation of these epicardial subplexuses, and/or nerves extending from these subplexuses, will cause an increase in contractility.

Exemplary Method for Increasing Contractility

Figure 9:
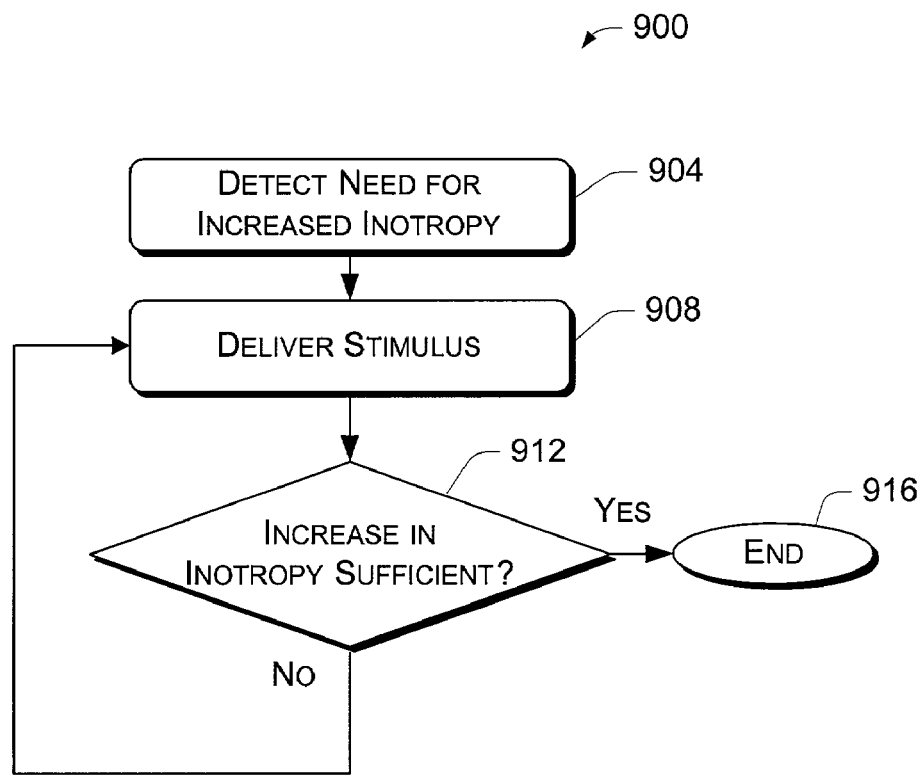
FIG. 9 is a block diagram of an exemplary method for stimulating left sympathetic nerves to increase inotropy.

FIG. 9 shows a block diagram of an exemplary method for stimulating sympathetic nerves 900 to increase contractility. In a detection block 904, a stimulation or other device determines a need for increased contractility. If a need exists, then, in a delivery block 908, a stimulation device delivers a stimulus to a sympathetic nerve associated with the left sympathetic trunk. The stimulus may be delivered via an electrode positioned in a vein, especially an epicardial vein, and/or in the pericardium using one or a variety of stimulation pulses. Optionally the electrodes may be placed directly epicardially during open chest surgery or through minimally invasive laproscopic procedures. The stimulation device optionally delivers the pulses during a refractory period to avoid direct electrical stimulation of the myocardium. In a post-stimulation block 912, the stimulation or other device determines whether and/or to what extent inotropy has increased. If the increase is sufficient, then the method 800 terminates in an end block 916. If the increase is insufficient, then the method 900 returns to the delivery block 908. The method 900 optionally includes a wait block between the delivery block 908 and the post-stimulation block 912 and/or between the post-stimulation block 912 and the return to the delivery block 908, in the case that the effect of the stimulation is insufficient. The device is further optionally programmable to make attempts at increasing and/or decreasing the pulse frequency, pulse width, pulse amplitude and/or other parameters. The exemplary method 900 may also account for other cardiac functions.

Coordinated Stimulation of Right and Left Sympathetic Pathways

In some circumstances, a device may stimulate sympathetic nerves of both right and left sympathetic trunks to increase heart rate and inotropy. For example, coordinated stimulation of right and left ventricles can optionally achieve a more desirable cardiac operation through selective adjustment of contractile force of right and/or left ventricles. In particular, output of the ventricles is determined primarily by preload, the contractile state of the myocardium, and the afterload, which all operate to produce a normal heart output of approximately 70 ml of blood per beat. Synergy of contraction refers to the normal harmonious, coordinated and efficient contractile process involving all chambers of the heart yielding optimal ejection of fluid. In a normal heart, the left ventricle ejects about 60% of its end-diastolic volume and the right ventricle ejects about 50% of its end-diastolic volume.

FIG. 10 shows a block diagram of an exemplary method 1000 for coordinated adjustment of heart rate and/or inotropy. In a detection block 1004, a stimulation and/or other device determines a need for improved cardiac output. In a subsequent determination block 1008, the stimulation device determines whether to deliver a stimulus to nerves of a patient's right sympathetic pathways, left sympathetic pathways or both right and left sympathetic pathways. In addition, the determination block 1008 optionally determines timing, location, duration, frequency and/or amplitude of the stimulus. A right sympathetic pathways delivery block 1012 and a left sympathetic pathway delivery block 1016 follow the determination block 1008. The right delivery block 912 delivers a stimulus or stimuli to affect sympathetic nerves associated with the right sympathetic pathways and to increase heart rate while the left delivery block 1016 delivers a stimulus or stimuli to affect sympathetic nerves associated with the left sympathetic pathways to increase inotropy. Following delivery, the stimulation and/or other device determines, in a determination block 1020, whether cardiac output has improved. For example, if cardiac output has improved to a sufficient degree, then the method 1000 terminates in an end block 1024. However, if cardiac operation has not improved, then the method 1000 returns to, for example, the right and/or left stimulus determination block 1008.

Selecting and/or Positioning Leads and/or Electrodes

An exemplary method for selecting and/or positioning a lead and/or an electrode is optionally implemented during implantation and/or after implantation. For example, during an implantation procedure, a patient is optionally instrumented to monitor heart function. For example, heart rate may be monitored via an EKG and contractility via arterial pressure sensors (e.g., the time derivative of the pressure can provide a good measure of contractility). In this example, monitoring of cardiac function and/or other functions may occur through use of external instrumentation and/or through use of implanted leads and/or sensors.

Consider a situation wherein sympathetic tuning via sympathetic nerve stimulation aims to increase heart rate. In such a situation, an exemplary method includes adjusting pulse amplitude and/or pulse frequency to relatively high values, automatically or manually (e.g., an implantable device having a lead and/or electrode implantation, selection and/or positioning mode(s)). In this exemplary method, through use of stimulation pulses and monitoring of cardiac function and/or other functions, a lead and/or electrode is positioned during implantation to achieve an optimal and/or a satisfactory increase in heart rate (e.g., an increase of therapeutic value). In this exemplary method, for example, a physician may slowly move a lead throughout an appropriate region and deliver pulses until a desired increase in heart rate is seen maximally via monitoring.

In yet another exemplary method, a lead and/or an electrode are optionally positioned to increase contractility due to sympathetic nerve stimulation while at the same time minimizing stimulation effects on heart rate. Once a "sweet spot" is found, then pulse parameters are optionally adjusted to minimize electrical power consumption, for example, by previously mentioned exemplary methods.

Alternative or Conjunct to Sympathomimetics

Sympathomimetic drugs such as dobutamine and angiotensin II are known to increase heart rate and contractility (positive inotropic therapy), see, e.g., Levett, et al., "Cardiac augmentation can be maintained by continuous exposure of intrinsic cardiac neurons to a beta-adrenergic agonist or angiotensin II", *J. Surg. Res.,* 66(2): 167–173 (1996). However, according to Burger, et al., "Comparison of the occurrence of ventricular arrhythmias in patients with acutely decompensated congestive heart failure receiving dobutamine versus nesiritide therapy", *Am. J. Cardiol.,* 88(1): 35–39 (2001), ventricular arrhythmias, which are common in patients with congestive heart failure (CHF), may be exacerbated by positive inotropic therapy. Thus, various exemplary methods and/or stimulation devices presented herein pose a viable alternative and/or conjunct to administration of inotropic agents.

Conjunct to Sympathetic Blockade

Pharmacological approaches to blockade of the sympathetic system include inhibition of central sympathetic outflow (using central sympatholytics, e.g. rilmenidine, moxonidine), blockade of the catecholamine biosynthetic pathway (dopamine beta hydroxylase antagonists) and blockade of the cardiac effects of sympathetic activation (beta-adrenoceptor blocking agents), see, e.g., Krum, "Sympathetic activation and the role of beta-blockers in chronic heart failure", *Aust. NZ J. Med.,* 29(3): 418–427 (1999).

Beta-blockers aim to offset deleterious effects associated with sympathetic stimulation; however, they also diminish beneficial inotropic effects. Indeed, a high beta blocker level may lead to bradycardia, symptomatic hypotension, excessive fatigue, and/or progressive signs or symptoms of congestive heart failure. Under such circumstances, beta blocker dose reduction is typically necessary and/or administration of an inotropic agent, see, e.g., Shakar and Bristow, "Low-level inotropic stimulation with type III phosphodiesterase inhibitors in patients with advanced symptomatic chronic heart failure receiving beta-blocking agents", *Curr. Cardiol. Rep.,* 3(3): 224–231 (2001). However, these methods inherently require human intervention, which may take days or weeks. Consequently, under such circumstances a need exists to increase contractility in a more expeditious manner.

Thus, according to various exemplary methods and/or stimulation devices described herein, heart rate and/or inotropy are optionally controlled and/or increased in patients subject to sympathetic blockade therapy. For example, selective electrical stimulation of sympathetic nerves acts to increase local levels of norepinephrine to overcome local effects of blockade therapy. Indeed, use of such methods and/or devices can maintain the benefits or blockade while providing increased heart rate and/or inotropy when needed. In such patients, increased heart rate and/or inotropy are needed, for example, during times of physical exertion, including, but not limited to, sex. Such a use offers considerable benefits over administration of syapthomimetics, which act via the circulatory system because the former causes norepinephrine release in close proximity to the myocardium.

Post-Operative Treatment

The contractile state of the myocardium can be depressed in the early postoperative period, and especially after major repairs, is usually supported by catecholamine inotropic agents or phosphodiesterase inhibitors. The problem is exacerbated in transplant patients wherein sympathetic innervation plays a critical role. Cao, et al., "Relationship between regional cardiac hyperinnervation and ventricular arrhythmia", *Circulation,* 101: 1960–1969 (2000), suggested that "abnormally increased postinjury sympathetic nerve density may be in part responsible for the occurrence of ventricular arrhythmia and sudden cardiac death in these patients". To counteract such effects, various exemplary methods and/or stimulation devices are used to stimulate sympathetic pathways in conjunction with pacing and/or defibrillation therapy.

CONCLUSION

Although exemplary methods and/or devices have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods and/or devices.

What is claimed is:

1. A method for increasing cardiac output comprising:
    positioning a first electrode proximate to a left sympathetic nerve pathway and positioning a second electrode proximate to a right sympathetic nerve pathway;
    determining whether to increase heart rate or increase inotropy; and
    selectively delivering an electrical signal to the first electrode to increase inotropy or to the second electrode to increase heart rate.

2. The method of claim 1, wherein the positioning includes positioning the first electrode proximate to a left sympathetic nerve ganglion.

3. The method of claim 1, wherein the positioning includes positioning the second electrode proximate to a right sympathetic nerve ganglion.

4. The method of claim 1, wherein the positioning includes positioning the first electrode proximate to a left sympathetic epicardial nerve.

5. The method of claim 1, wherein the positioning includes positioning the second electrode proximate to a right sympathetic epicardial nerve.

6. The method of claim 1, wherein the positioning includes positioning the first electrode proximate to a left sympathetic cardiac nerve.

7. The method of claim 1, wherein the positioning includes positioning the second electrode proximate to a right sympathetic cardiac nerve.

8. The method of claim 1, wherein the positioning includes positioning the first electrode proximate to an epicardial plexus innervated by a left sympathetic nerve.

9. The method of claim 1, wherein the positioning includes positioning the second electrode proximate to an epicardial plexus innervated by a right sympathetic nerve.

10. The method of claim 1, wherein the delivering delivers an electrical signal to the first electrode to stimulate a left sympathetic nerve and thereby increase inotropy.

11. The method of claim 1, wherein the delivering delivers an electrical signal to the second electrode to stimulate a right sympathetic nerve and thereby increase heart rate.

12. The method of claim 1, wherein the delivering delivers an electrical signal to the first electrode to stimulate a left sympathetic nerve and thereby increase inotropy and delivers an electrical signal to the second electrode to stimulate a right sympathetic nerve and thereby increase heart rate.

13. The method of claim 1, wherein the electrical signal includes parameters, the parameters selected from the group consisting of amplitude, frequency, voltage, current, energy, charge, power, and pulse width.

14. One or more computer-readable media having computer-readable instructions thereon which, when executed by a programmable stimulation device, causes a stimulation device to execute the delivering of claim 1.

15. A method for increasing cardiac output comprising:
detecting a need for increased cardiac output;
determining whether to increase heart rate or increase inotropy or both; and
selectively delivering electrical signals to a first electrode proximate to a left sympathetic nerve pathway to increase inotropy or to a second electrode proximate to a right sympathetic nerve pathway to increase heart rate.

16. The method of claim 15, wherein the first electrode is proximate to a left sympathetic nerve ganglion.

17. The method of claim 15, wherein the second electrode is proximate to a right sympathetic nerve ganglion.

18. The method of claim 15, wherein the first electrode is proximate to a left sympathetic epicardial nerve.

19. The method of claim 15, wherein the second electrode is proximate to a right sympathetic epicardial nerve.

20. The method of claim 15, wherein the first electrode is proximate to a left sympathetic cardiac nerve.

21. The method of claim 15, wherein the second electrode is proximate to a right sympathetic cardiac nerve.

22. The method of claim 15, wherein the first electrode is proximate to an epicardial plexus innervated by a left sympathetic nerve.

23. The method of claim 15, wherein the second electrode is proximate to an epicardial plexus innervated by a right sympathetic nerve.

24. The method of claim 15, wherein the delivering delivers an electrical signal to the first electrode to stimulate a left sympathetic nerve and thereby increase inotropy.

25. The method of claim 15, wherein the delivering delivers an electrical signal to the second electrode to stimulate a right sympathetic nerve and thereby increase heart rate.

26. The method of claim 15, wherein the delivering delivers an electrical signal to the first electrode to stimulate a left sympathetic nerve and thereby increase inotropy and delivers an electrical signal to the second electrode to stimulate a right sympathetic nerve and thereby increase heart rate.

27. The method of claim 15, wherein the electrical signal includes parameters, the parameters selected from the group consisting of amplitude, frequency, voltage, current, energy, charge, power, and pulse width.

28. One or more computer-readable media having computer-readable instructions thereon which, when executed by a programmable simulation device, causes a simulation device to execute the method of claim 15.

* * * * *